US008261910B2

(12) United States Patent
Guenter et al.

(10) Patent No.: US 8,261,910 B2
(45) Date of Patent: Sep. 11, 2012

(54) PACKAGE HOUSING FOR AN ELONGATE OBJECT

(75) Inventors: Daniel Guenter, Basel (CH); Gideon Brunner, Basel (CH)

(73) Assignee: Straumann Holding AG, Basel (CH)

( * ) Notice: Subject to any disclaimer, the term of this patent is extended or adjusted under 35 U.S.C. 154(b) by 69 days.

(21) Appl. No.: 12/873,515

(22) Filed: Sep. 1, 2010

(65) Prior Publication Data

US 2011/0056850 A1      Mar. 10, 2011

(30) Foreign Application Priority Data

Sep. 4, 2009   (EP) ...................................... 09011364

(51) Int. Cl.
   *B65D 85/28*   (2006.01)
(52) U.S. Cl. ........................................ 206/363; 206/438
(58) Field of Classification Search .................. 206/363, 206/364, 438, 368, 379; 433/77
   See application file for complete search history.

(56) References Cited

U.S. PATENT DOCUMENTS

| 4,413,731 | A   |   | 11/1983 | Weideman |         |
|-----------|-----|---|---------|----------|---------|
| 4,445,611 | A   | * | 5/1984  | Shofu    | 206/369 |
| 4,664,259 | A   | * | 5/1987  | Landis   | 206/365 |
| 5,775,499 | A   |   | 7/1998  | Budert   |         |
| 6,969,197 | B2  | * | 11/2005 | Sedley   | 383/200 |
| 2001/0008215 | A1 |   | 7/2001 | Colombo |         |
| 2006/0283769 | A1 |   | 12/2006 | Roesler |         |
| 2008/0185305 | A1 |   | 8/2008 | Roesler |         |

FOREIGN PATENT DOCUMENTS

| DE | 3633664 A1    | 4/1988  |
|----|---------------|---------|
| DE | 102005022385 A1 | 11/2006 |
| DE | 102007005515 B3 | 8/2008  |
| GB | 2335911 A     | 10/1999 |

OTHER PUBLICATIONS

European Search Report dated Mar. 5, 2010 in corresponding EP 09011364.8-2308.

\* cited by examiner

*Primary Examiner* — David Fidei
(74) *Attorney, Agent, or Firm* — Rissman Hendricks & Oliverio LLP

(57) ABSTRACT

Package housing for an elongate object (8), including a base element (2) having a housing wall (6) defining a receptacle (4) for the object (8), wherein the receptacle (4) has a longitudinal axis (L) which runs substantially coaxially to the longitudinal axis of the object (8) in the packed state. The base element (2) comprises a head part (10) and a holding part (12) arranged in the direction of the longitudinal axis (L) next to the head part (10), which holding part is connected to the head part (10) by a weakening zone (30) and including at least one holding portion (34), which is intended to hold the object (8) in the holding part (12). According to the invention, the weakening zone (30) is a predetermined breaking point (32). The holding portion (34) includes at least one spacer (42*a*, 42*b*), which is configured such that the object (8), in the packed state, is held in a contact-free manner with respect to that part of the housing wall (6) of the holding part (12) which extends in the direction of the longitudinal axis (L).

19 Claims, 11 Drawing Sheets

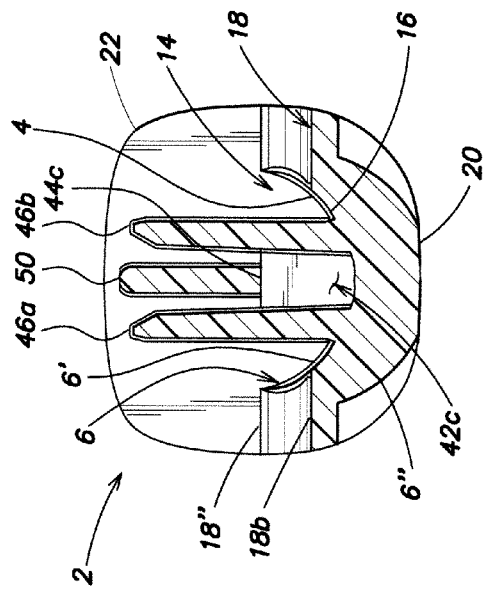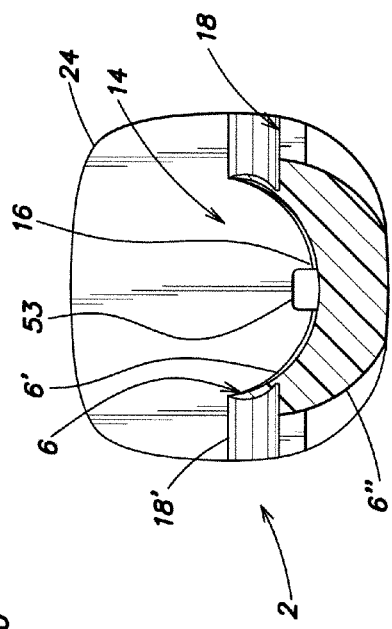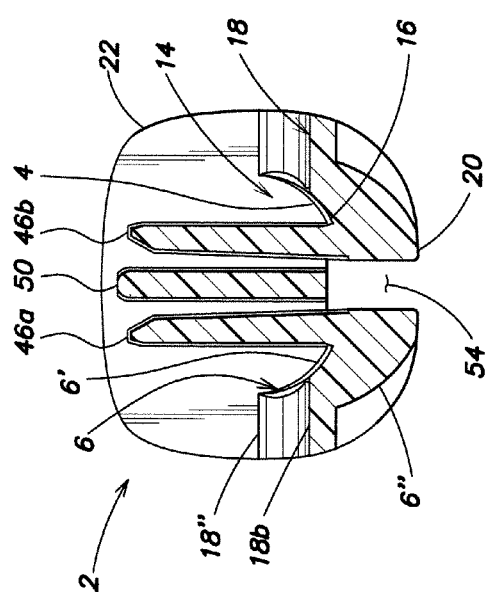

PACKAGE HOUSING FOR AN ELONGATE OBJECT

FIELD OF THE INVENTION

The present invention relates to a package housing for an elongate object, use of the package housing for a drill attachment, in particular a dental drill attachment, and a packaging arrangement comprising the package housing and the elongate object.

BACKGROUND

Package housings for elongate objects, such as, for instance, drill attachments, have long been known. By way of example, reference is made in this regard to U.S. Pat. No. 5,775,499 and to US-A-2001/0008215, in which a packaging suitable, inter alia, for drills (drill attachments) is described.

Dental drill attachments, because of their fragility, place especially high demands upon their packaging. This packaging should ensure that the dental implant drill, for example, remains intact even if the packaging falls to the floor.

In addition, such dental drill attachments must be kept sterile with respect to their use. In order to ensure sterility, on the one hand at least the drill tip, i.e. the part which comes into contact with the tissue of the patient, should be kept under sterile conditions until shortly before use. On the other hand, it should be possible to remove the drill attachment from the packaging without the cutting region of the drill (the "bit") being touched.

Correspondingly, in DE-A-102005022385 there is described an individual packaging unit for fragile articles, which has a base containing an upwardly directed receiving bore in which the foot of the fragile article is inserted and projects in a self-supporting manner. The fragile article is here protected by means of a protective cap. The packaging described in DE-A-102005022385 is foldable about an axis running transversely to the longitudinal axis, the article to be protected being freely accessible in the course of the folding.

This packaging has the drawback, however, that, due to the arrangement of the drill in the packaging, the base and the receiving bore must be ultraclean in order to prevent unwanted contamination of the article. This necessitates, on the one hand, a suitable choice of material for the packaging, while, on the other hand, the production of the packaging must take place under clean-room conditions, which is often associated with a relatively high cost. Furthermore, the visual perceptibility of the packed article is restricted, since it is sunk in a receiving bore. A resultant blunder, specifically in connection with dental drill attachments, is particularly undesirable however, since sterility can no longer be ensured once the sterile barrier has been broken open and the dental drill attachment must therefore be discarded.

SUMMARY OF THE INVENTION

The object of the present invention is thus to provide a package housing for an elongate object, which allows at least parts of the object to be kept clearly visible from the outside and under sterile conditions and which at the same time—without restriction with respect to the material used for the production—makes it possible to prevent contamination of said parts, including as the object is removed.

The base element is of substantially dimensionally stable configuration and serves as a carrier for the object to be packed. The receptacle defined by the housing wall of the base element here has a longitudinal axis which runs substantially coaxially to the longitudinal axis of the object in the packed state.

The base element comprises a head part and a holding part arranged in the direction of the longitudinal axis next to the head part, which holding part is connected to the head part by a weakening zone. The holding part here comprises at least one holding portion, which is intended to hold in the holding part the object to be packed.

According to the invention, the weakening zone is a predetermined breaking point.

The package housing according to the invention allows the whole of the packed object to be kept clearly visible from the outside and under sterile conditions until shortly before its removal. For the removal, the package housing is broken at its predetermined breaking point. After the head part has been broken off, the packed object held by the holding portion projects in a self-supporting manner with a first proximal end region from the exposed end of the holding part, while the distal end region of the object, lying opposite the proximal end region, is in the holding part and can thus be kept, as before, under sterile conditions. The object can now be removed from the holding part by gripping of the proximal end region; touching of the sterile, distal end region of the object is thus unnecessary.

In addition, the holding part includes at least one spacer, which is configured such that the object, in the packed state, is held in a contact-free manner with respect to that part of the housing wall of the holding part which extends in the direction of the longitudinal axis. This ensures that the object is kept away from possible contaminations which can arise upon contact with the housing wall. This is especially relevant in connection with a packed drill attachment, since an abrasion can arise between the sharp-edged drill thread of the drill tip and the housing wall and the material chips which are hereby formed can contaminate the drill tip.

As mentioned, the package housing of the present invention is especially suitable for objects which must be kept sterile, at least in some areas, and should come into contact with a non-sterile foreign component merely at that point at which gripping is unavoidable. The elongate packing object is here arranged such that the distal end region to be kept sterile is disposed in the holding part and the gripped, proximal end region is disposed in the head part. In the case of a (dental) drill attachment, for which the package housing of the present invention is especially suitable, the drill tip is thus disposed in the holding part and the drill shank to be connected to the drill is disposed in the head part.

Normally, the predetermined breaking point runs substantially at right angles to the longitudinal axis of the receptacle, which enables the head part to be broken off from the holding part in the simplest possible manner.

The predetermined breaking point can be present, for instance, in the form of connecting points, which respectively form a bridge and are formed of brittle material. In this preferred embodiment, the predetermined breaking point thus comprises at least one bridge, which breaks in the case of a predefined bending angle between the head part and the holding part. The bending angle here lies, particularly preferably, between 45° and 90°.

As can be seen, in particular, also from the figures, the at least one spacer is configured in the form of a protrusion protruding from the receptacle, which protrusion forms a support surface for the object to be packed. In this embodiment, a very efficient spacer configuration can be achieved, for instance, if the protrusion protrudes at the deepest point of the receptacle. The number of spacers, or their distance apart, can vary according to the object.

In order to keep the contact surface between the object to be packed and the base element as small as possible for the abovementioned reasons, the holding part comprises just a single holding portion. This is preferably disposed in a region adjoining the predetermined breaking point. The distance between the holding portion and the gripped region can thereby be reduced, which enables the gripped object to be released from the holding portion and removed from the holding part with relatively little effort.

Preferably, the holding portion is configured such as to hold the object by means of a snap-locking connection. Particularly preferably, the holding portion comprises two elastic snap-locking lips arranged lying opposite each other about the longitudinal axis of the receptacle. For the removal of the object, this is moved in the direction away from the receptacle, whereupon the snap-locking lips are laterally deflected and, following the removal of the object, spring back again. Preferably, the pull-off force to be expended for the removal is between 3 and 6 N.

A particularly stable arrangement of the object in the package housing can be made possible by the fact that the base element, at the ends lying opposite each other with respect to the longitudinal axis of the receptacle, respectively comprises an end wall lying in a plane running at right angles to the longitudinal axis. The object can thereby be additionally secured against displacement in the longitudinal direction.

A further securement of the object can be ensured by the fact that the end wall of the head part has a guide which tapers in the direction of the receptacle and which is configured such that the object is held by means of a clamping action.

As mentioned, the package housing according to the invention is especially suitable for objects which, at least in some areas, should be kept sterile. Correspondingly, according to a particularly preferred embodiment, the inside of the package housing is sterile.

Normally, the receptacle, with the object accommodated therein, is protected with a cover. In order to ensure the visibility of the object from the outside, the receptacle is covered, particularly preferably, by a see-through packaging film, whereby a blister package housing results.

According to a further aspect, the invention additionally relates to a packaging arrangement comprising the described package housing and an elongate object, in particular a drill attachment. If a drill attachment is present as the packed object, then it is possible according to the invention to remove this from the package housing without touching the bit.

Normally, the shape of the receptacle is matched to the shape of the elongate object to be packed; in the case of a drill attachment as the object to be packed, the head part and/or the holding part is/are therefore preferably configured substantially in the form of a trough.

In order to ensure an optimal gripping and holding of the package housing, the base element can comprise on both sides a respective side wall portion running in the direction of the longitudinal axis. On this side wall portion, ribs can be arranged on the outer wall side with a view to giving optimal grip.

The base element according to the present invention is normally made of plastic. According to use or according to the configuration of the predetermined breaking point, the material can exhibit enhanced flexibility or brittleness.

Typically, the base element of the present invention is produced by injection molding. For this reason, the base element has depressed regions for the injection points.

BRIEF DESCRIPTION OF THE DRAWINGS

The invention is explained in detail with reference to the figures, of which:

FIG. 5 shows the base element shown in FIG. 1, in cross section along the line 5-5 in FIG. 2;

FIG. 6 shows the base element shown in FIG. 1, in cross section along the line 6-6 in FIG. 2;

FIG. 7 shows the base element shown in FIG. 1, in cross section along the line 7-7 in FIG. 2;

DETAILED DESCRIPTION

Figure 1:
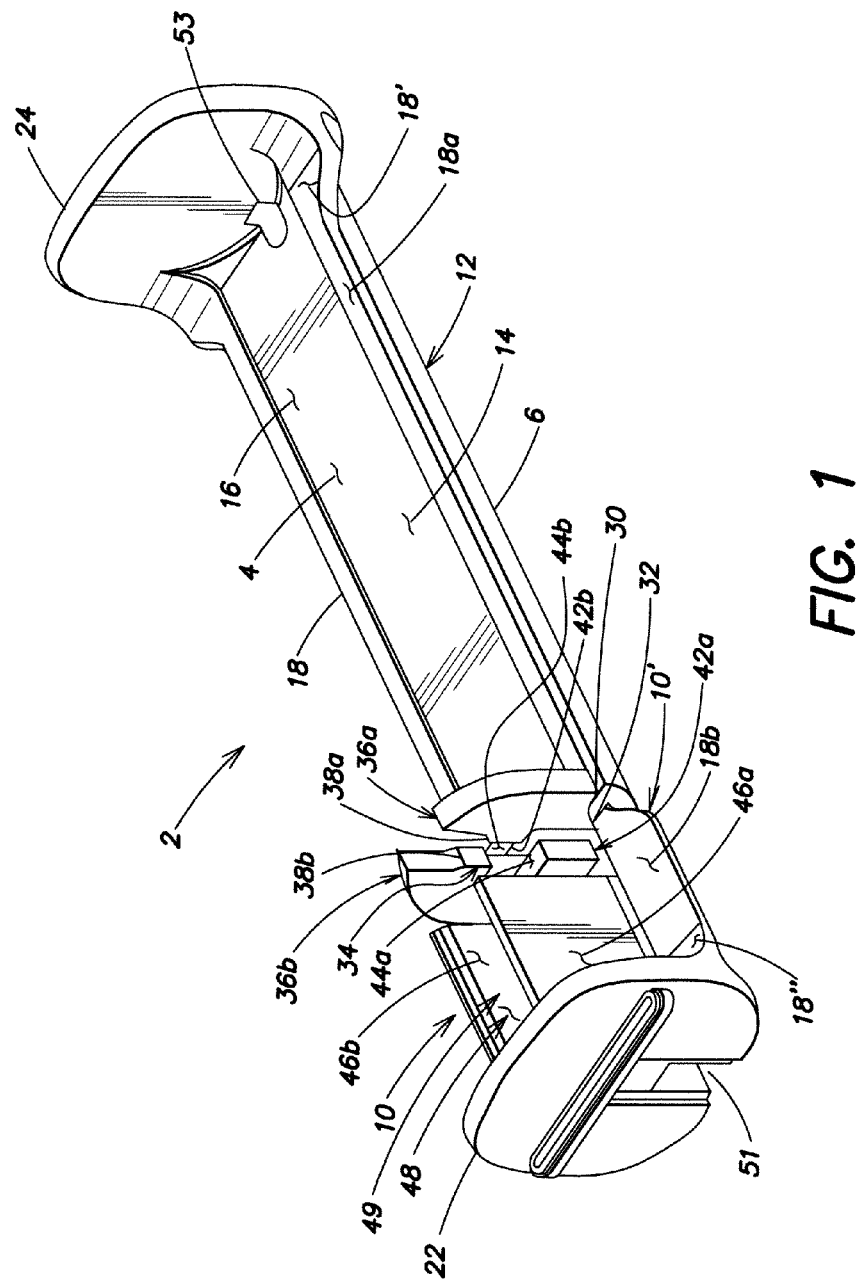
FIG. 1 shows a perspective representation of a base element of a package housing according to one embodiment of the invention, in which the weakening zone is configured in the form of a predetermined breaking point.

The base element 2 according to the embodiment shown in FIGS. 1 to 11 and 13 has a housing wall 6 defining a receptacle 4 for an object. The receptacle 4 has a longitudinal axis L shown in FIG. 3, which runs substantially coaxially to the longitudinal axis of the object 8 in the packed state, as is apparent, moreover, from FIG. 13.

The base element 2 comprises a head part 10 and a holding part 12 arranged in the direction of the longitudinal axis L next to the head part 10. The holding part 12 is here configured longer than the head part 10. In the shown embodiment, the ratio of the extent of the holding part 12 in the longitudinal direction to the corresponding extent of the head part is about 3:1. Any other ratio suitable for the present purposes is also conceivable, however.

Both the head part 10 and the holding part 12 are configured substantially in the form of a trough 14 having a cross-sectionally sickle-shaped trough floor 16 and a trough rim 18 protruding horizontally outward, as can be seen, in particular, from FIGS. 5 and 6. The inner side 6' of the housing wall 6 of the base part 2 thus has a substantially round curvature. In order to ensure that the package housing can be placed stably onto a flat foundation, the outer side 6" of the trough floor 16 has a corresponding flattening 20. As can be seen, for instance, from FIGS. 5 and 6 in comparison with FIGS. 7 and 9, the cross-sectional profile of the trough floor 16 of the head part 10 is substantially congruent with that of the holding part.

At the ends which lie opposite each other with respect to the longitudinal axis L, the base element 2 respectively comprises an end wall lying in a plane running at right angles to the longitudinal axis. At the free end of the head part 10 there is arranged a first, proximal end wall 22, while at the free end of the holding part 12 there is arranged a second, distal end wall 24, which lies in a plane running substantially parallel to the proximal end wall 22. Both end walls 22, 24 are configured—as, for example, in FIGS. 5, 6 and 8, and 7 and 9—roughly in the form of a round-cornered trapezoid, substantially congruent to each other.

Figure 2:
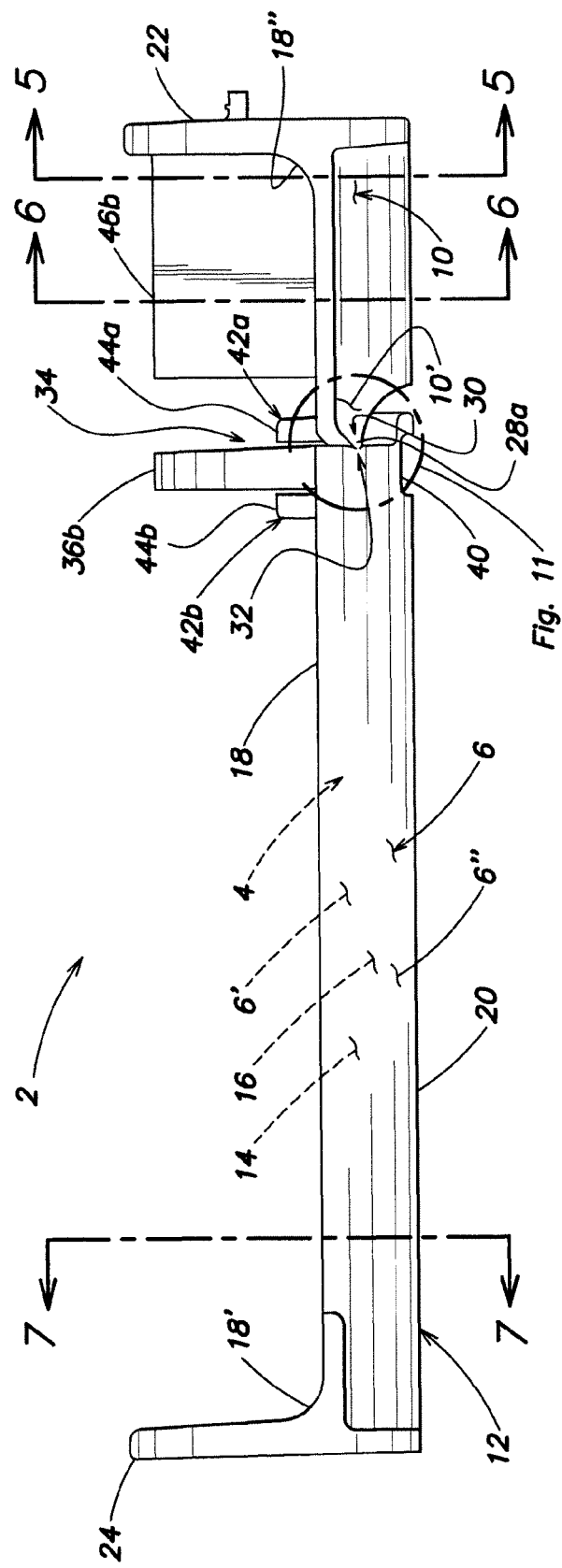
FIG. 2 shows a plan view of the longitudinal side of the base element shown in FIG. 1.
Figure 3:
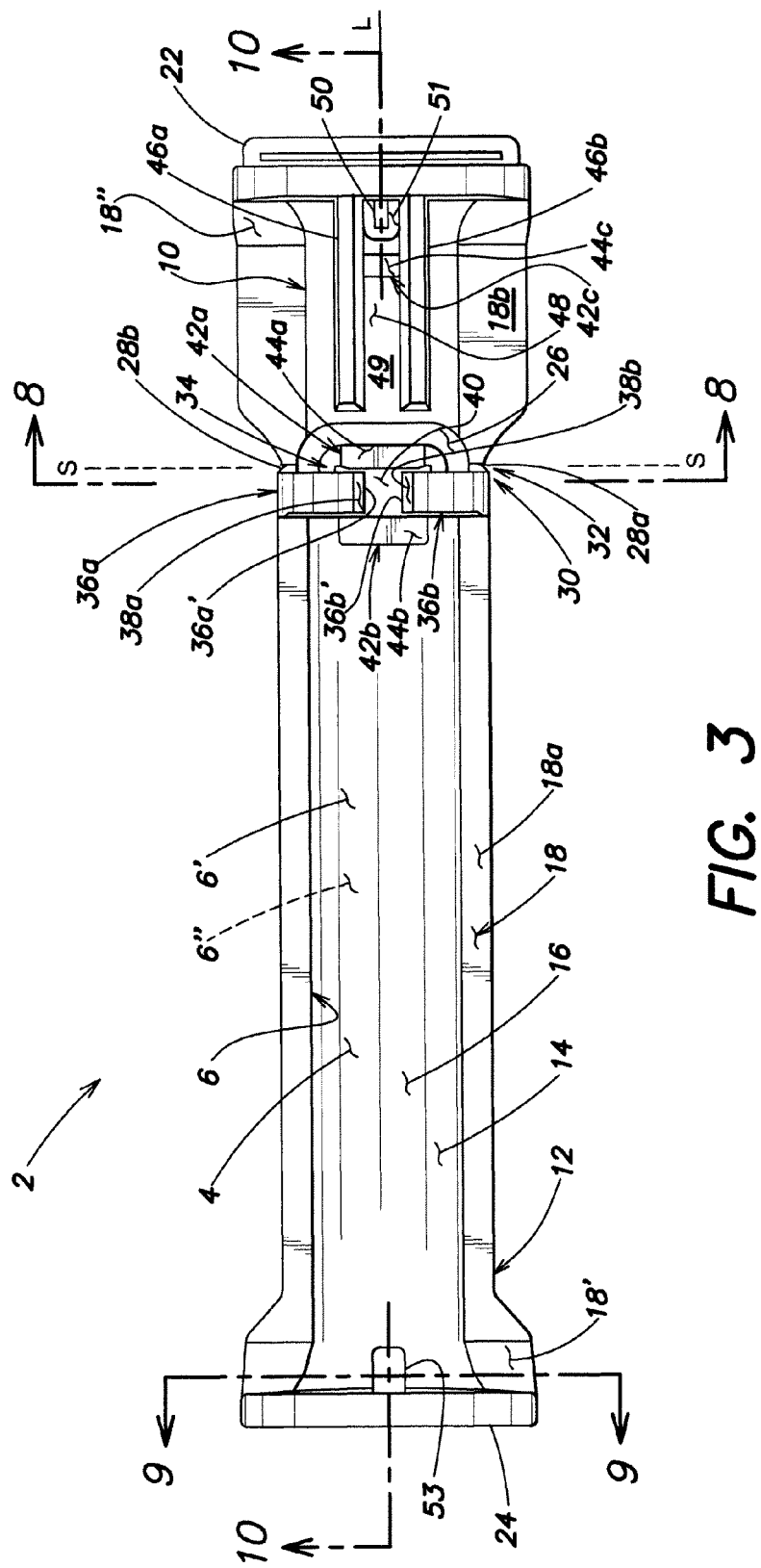
FIG. 3 shows a plan view of the base element shown in FIG. 1, from above.
Figure 4:
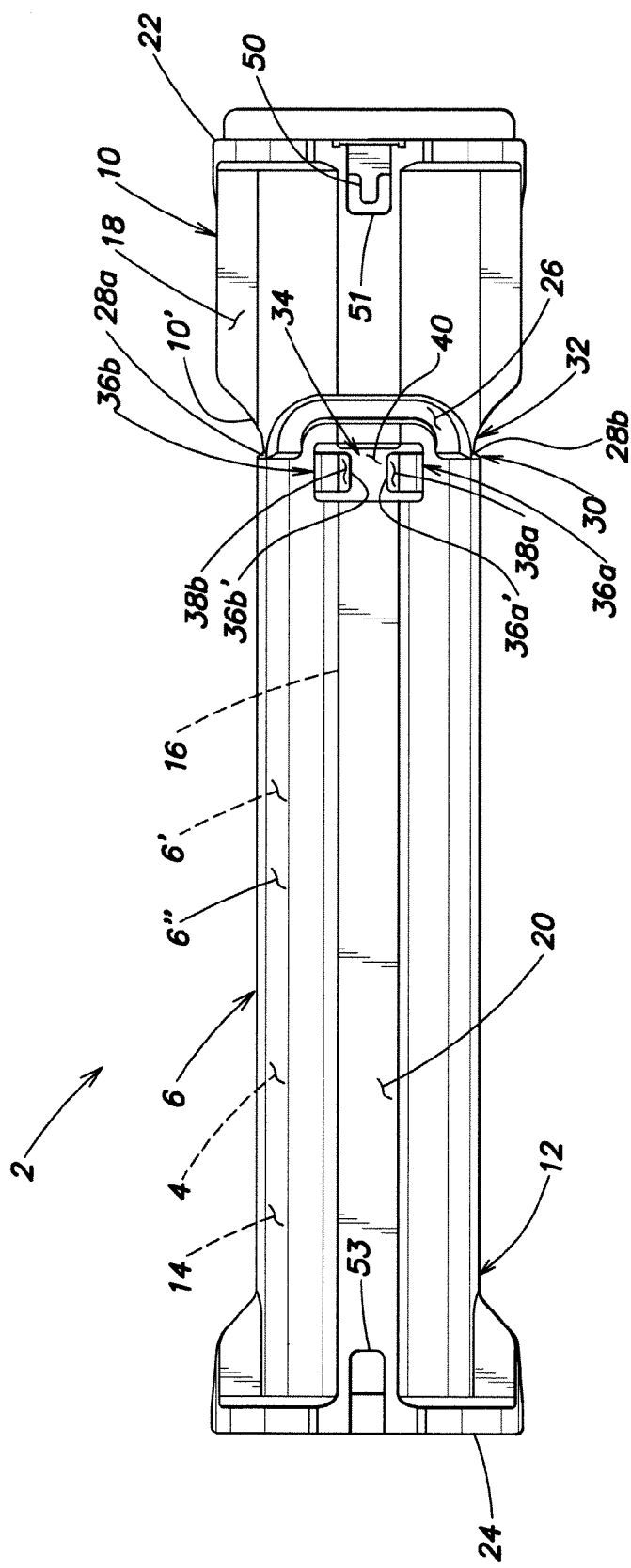
FIG. 4 shows a plan view of the base element shown in FIG. 1, from below.
Figure 8:
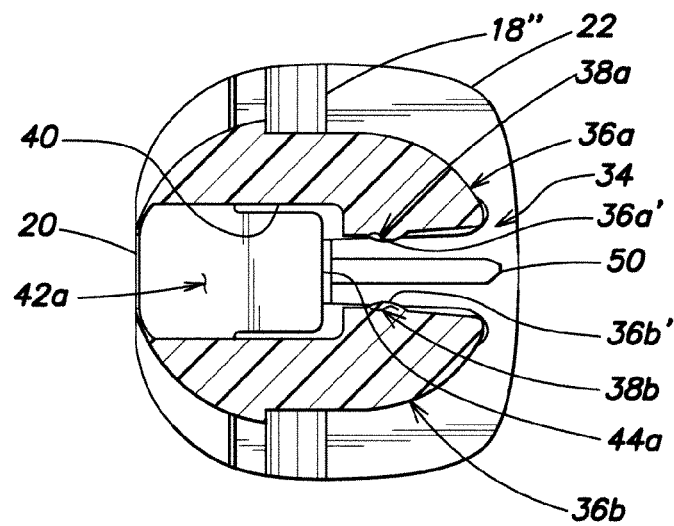
FIG. 8 shows the base element shown in FIG. 1, in cross section along the line 8-8 in FIG. 3.

As can be seen, in particular, from the width profile shown in FIG. 3, the trough rim 18 of the holding part 12 widens, in the distal end region 18' adjacent to the distal end wall 24, toward the distal end wall 24. At its widest point, the width of the trough rim portion 18a of the holding part 12 substantially corresponds to the width of the trough rim portion 18b of the head part 10. Both in the distal end region 18' and in the proximal end region 18", the trough rim, as is shown in the thickness profile shown in FIG. 2, is curved on the inside such that it merges fluently into the respective end wall 24 and 22.

In that region 10' of the head part 10 which adjoins the holding part 12, the trough rim 18 tapers toward the holding part 12. As is shown, moreover, from FIGS. 2 and 11, the head part 10 tapers in this region also in terms of thickness; the inner side of the trough floor 16 is configured convexly curved in said region. As can be seen, in particular, from FIG. 3, a gap 26 is configured in the connecting region between the holding part 12 and the head part 10, so that the connection is realized merely by means of two connecting points, which respectively form a bridge 28a and 28b.

The two bridges 28a, 28b lie in a weakening zone 30 and form a swivel axis S about which the head part 10 can be deflected out of the direction of the longitudinal axis L. At least in this weakening zone 30, the material of the base element 2 is brittle, so that a relatively slight deflection leads already to breaking of the connection. In the shown embodiment, the weakening zone 30 thus forms a predetermined breaking point 32.

Directly at that region of the holding part 12 which adjoins the weakening zone 30 there is arranged a holding portion 34 protruding from the trough floor 16. This holding portion comprises two elastic snap-locking lips 36a, 36b, which are arranged around the longitudinal axis L and which, on their inner side 36a', 36b' facing the longitudinal axis L, respectively have a boss 38a and 38b. The snap-locking lips 36a, 36b are configured such that, upon introduction of the object to be packed, they are laterally deflected and, following surmounting of the bosses 38a, 38b, elastically spring back, whereby a latching engagement and thus stable holding of the elongate object is ensured. In order to prevent the trough floor 16 from being overstressed upon the lateral deflection of the snap-locking lips 36a, 36b, said trough floor has between the snap-locking lips 36a, 36b an opening 40.

The snap-locking lips 36a, 36b are flanked on both sides, in the direction of the longitudinal axis L, by a centrally arranged spacer 42a and 42b respectively. These each form a support surface 44a and 44b for the elongate object. As can be seen, in particular, from FIG. 3, the gap 26 is of substantially U-shaped configuration, the spacer 42a arranged on the side facing the head part 10 ending up between the legs of the U.

In addition, the proximal end wall 22 has two protrusions 46a, 46b extending almost over the entire length of the head part. These define a groove 48, which serves as a guide 49 for the elongate object. The groove 48 is configured such that it tapers gently in the direction of the trough floor 16, which ensures that the elongate object is held, in addition to the snap-locking connection realized by means of the holding portion 34, also by clamping action. Between the protrusions 46a, 46b there is arranged a further spacer 42c protruding from the trough floor 16 of the head part 10, which further spacer forms a further support surface 44c for the object to be packed. In addition, between the protrusions 46a, 46b there is arranged a molding 50 protruding from the proximal end wall 22, which molding serves as a spacer between the proximal end wall 22 and the proximal end of the object to be packed.

Figure 9:
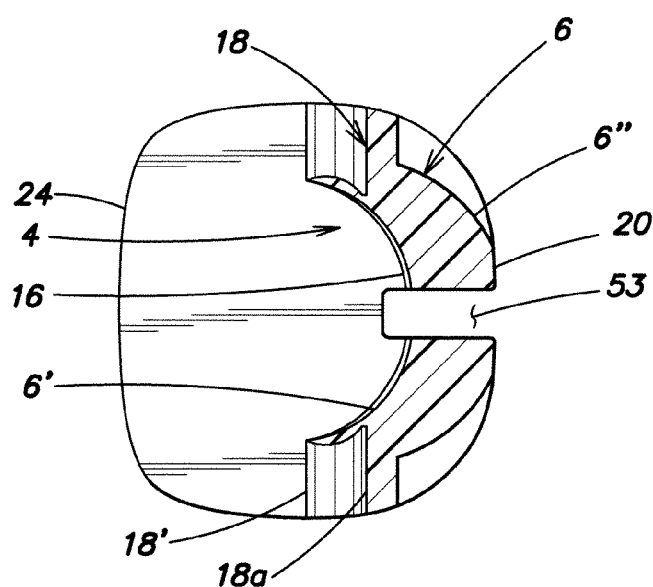
FIG. 9 shows the base element shown in FIG. 1, in cross section along the line 9-9 in FIG. 3.
Figure 10:
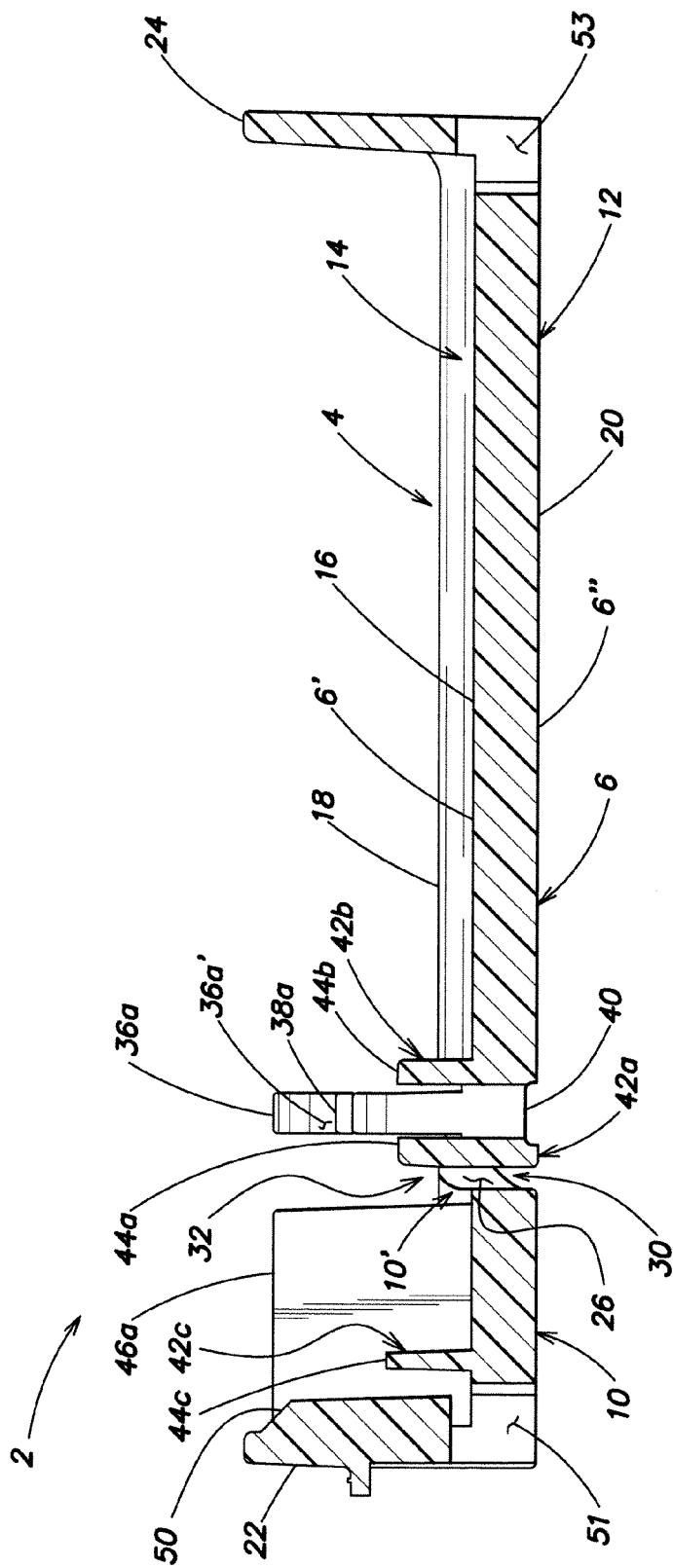
FIG. 10 shows the base element shown in FIG. 1, in cross section along the line 10-10 in FIG. 3.
Figure 11:
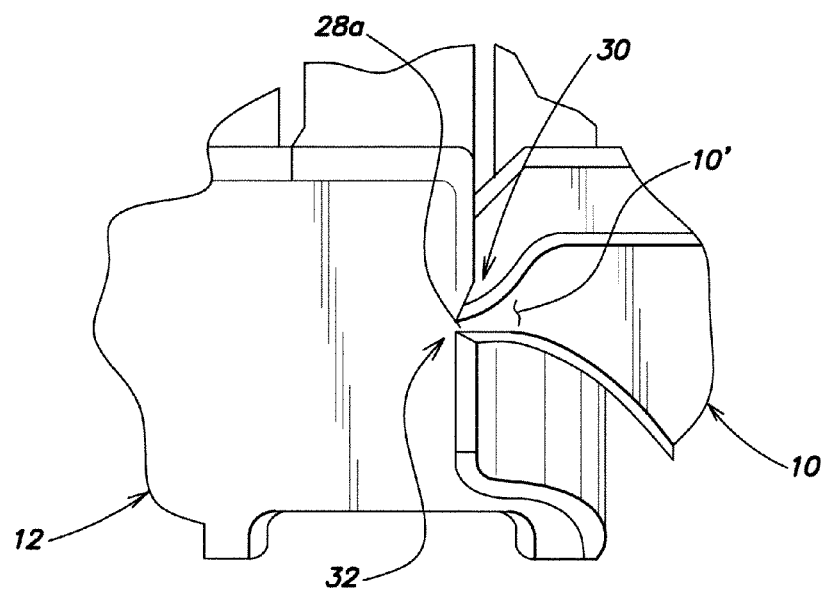
FIG. 11 shows an enlarged view of the detail X area (shown labelled FIG. 11 in FIG. 2), in which the predetermined breaking point is shown in detail.

As can be seen in particular, for instance, from FIGS. 5, 9 and 10, the base element 2 has both in the proximal end region and in the distal end region a centrally arranged opening 51 and 53 for drainage of the receptacle 4 following cleaning of the object.

When an object is introduced into the base part 2, the proximal end region of the object is thus guided in the groove 48 of the head part. At the same time, the snap-locking lips 36a, 36b of the holding part 12 are laterally deflected and, following surmounting of the bosses 38a, 38b, elastically spring back, whereby a latching engagement, and thus stable holding, of the elongate object is ensured. The object can then, together with the base part 2, be provided with a protective cover, such as, for instance, a see-through packaging film 3 (FIG. 13).

In order to remove the object, the head part 10 is broken off from the holding part 12, whereafter, by virtue of the arrangement of the spacers 42a, 42b of the holding part 12 and of the holding portion 34, the object projects in a self-supporting manner from the holding part 12. The object can be gripped by this projecting proximal end region 22 without jeopardizing the sterility of the distal end region disposed in the holding part 12. In the case of a drill attachment packed in a package housing according to the invention, it is thus possible to remove this without touching the bit.

Figure 12:
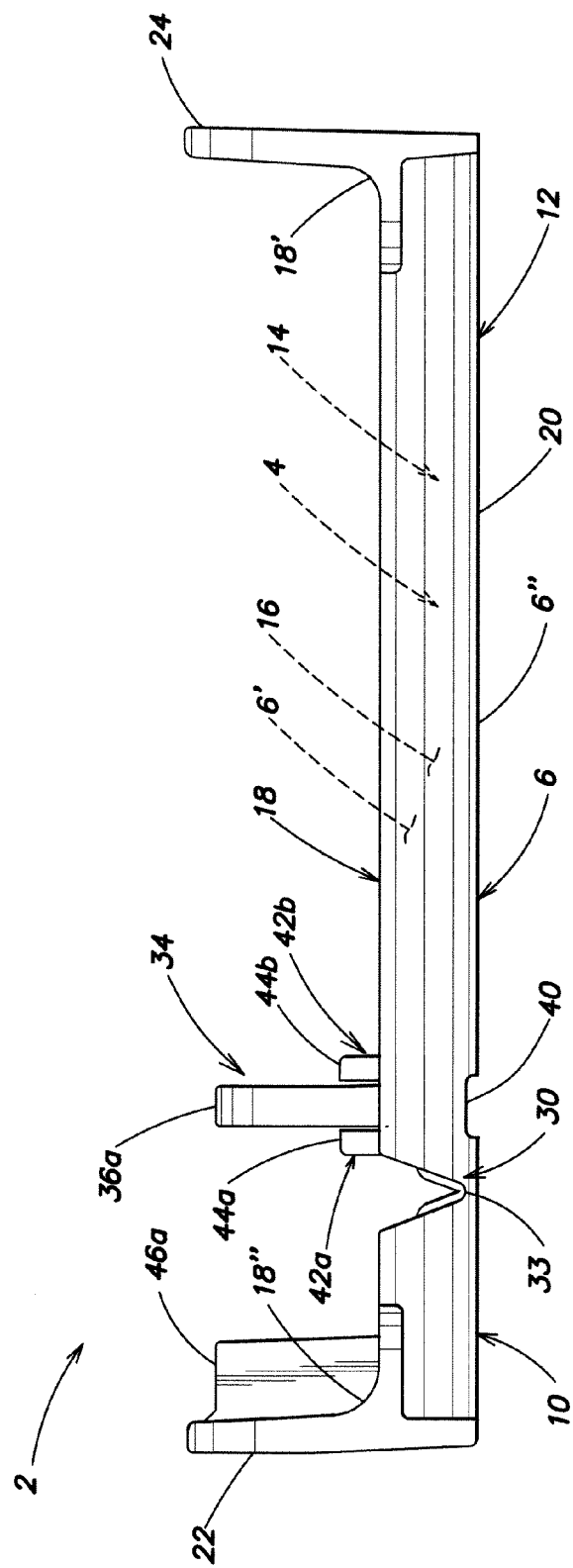
FIG. 12 shows a plan view of the longitudinal side of a base element having a folding zone in place of a predetermined breaking point.

In contrast to the weakening zone according to that embodiment according to the present invention which is shown in FIGS. 1 to 11, in the base element shown in FIG. 12 the connecting zone between the head part 10 and the holding part 12 is configured as a continuous surface and thus as a folding zone 33.

Figure 13:
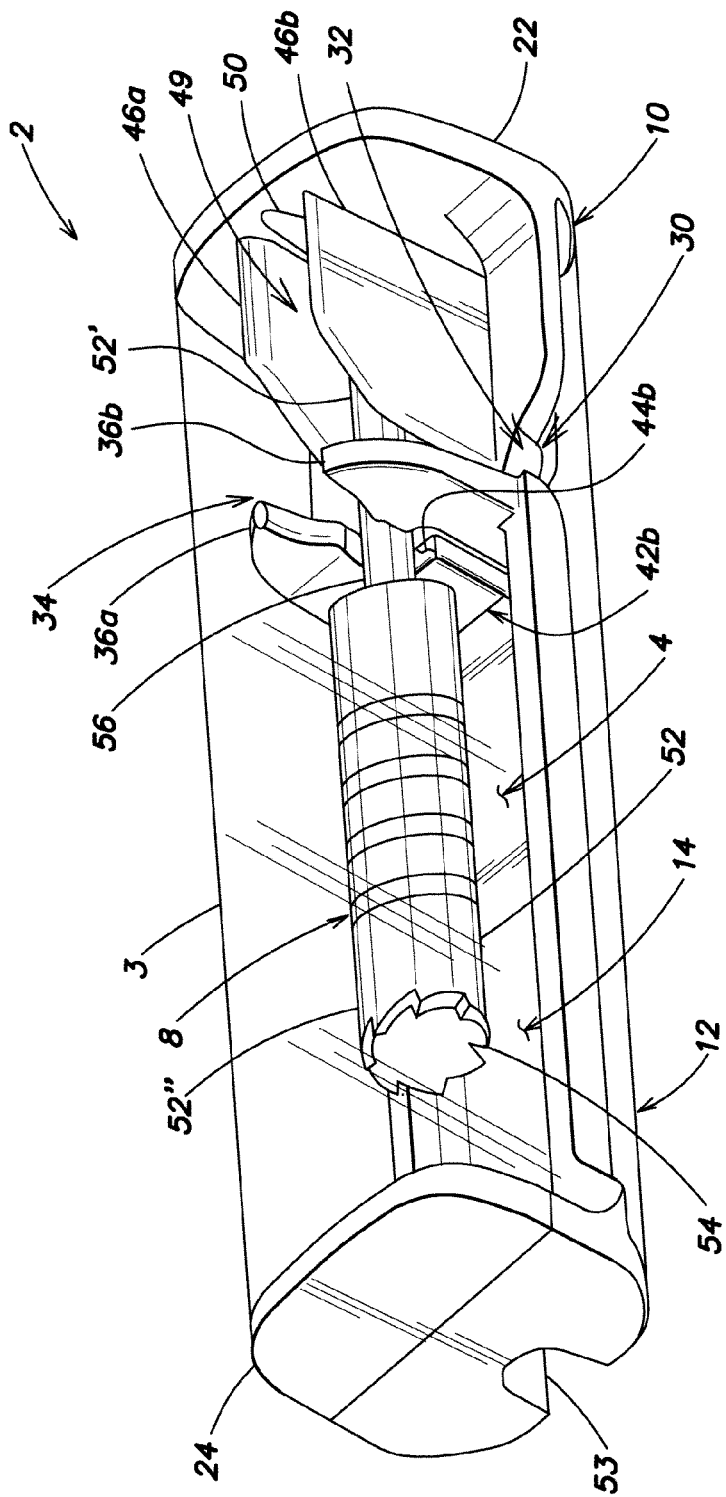
FIG. 13 shows a perspective representation of the base element shown in FIG. 1, with a drill attachment held by this.

As is shown in FIG. 13, the object 8 can be constituted by a drill attachment 52, whereof the proximal, i.e. drill-facing end region 52' is disposed in the head part and the distal end region 52", having the drill tip 54 with the drill thread (not shown), is disposed in the holding part 12. The drill attachment 52 is here held by its shank 56 by the holding portion 34 or fixed by means of the guide 49 in the head part 10. For the removal of the drill attachment, the head part 10 is broken off, whereafter the drill attachment 52 projects with its proximal end region 52' in a self-supporting manner from the holding part 12 and can be connected to the drill. The drill attachment 52 which is in this way fastened to the drill can then be removed from the holding part 12 without the distal end region 52" of the drill attachment 52 being touched.

Figure 14:
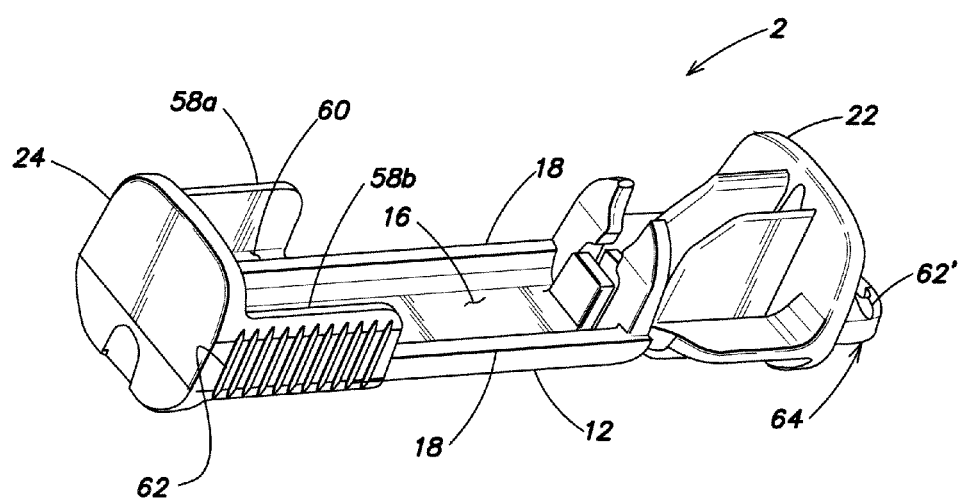
FIG. 14 shows a perspective representation of a base element of a further embodiment of the present invention.

The base element 2 shown in FIG. 14 differs from that according to FIGS. 1 to 11 and 13 essentially in that it comprises on both sides a respective side wall portion 58a, 58b adjoining the distal end wall 24 and running in the direction of the longitudinal axis L. The respective side wall portion 58a and 58b here runs in a plane running substantially at right angles to the plane of the trough rim 18 and is connected to the trough rim 18 by a web 60, which merges into said trough rim. In the shown embodiment, the side wall portions 58a, 58b extend over a length which is somewhat less than half the length of the holding part 12.

Arranged on the outer side of the side wall portions 58a, 58b are ribs 62, which in the shown embodiment run at right angles to the longitudinal axis L. The ribs contribute to an enhanced grip of the base element 2 or of the package housing.

Moreover, the base element shown in FIG. 14 differs from that shown in FIGS. 1 to 11 and 13 in that on the proximal end wall 22 there is configured a projection 64, which runs in a plane arranged parallel to the plane of the trough rim 18 or of the trough floor 16. The projection 64 too helps to make the base element 2 or the package housing able to be optimally gripped and held, and preferably has ribs 62' for this purpose.

The invention claimed is:

1. A package housing for an elongate object having a longitudinal object axis, the package housing comprising
    a base element having a housing wall defining a receptacle for the object, wherein the receptacle has a longitudinal receptacle axis which runs substantially coaxially to the longitudinal object axis in the packed state and the base element comprises a head part and a holding part arranged in the direction of the longitudinal receptacle axis next to the head part,
    the holding part is connected to the head part by a weakening zone comprising a predetermined breaking point, and
    the holding part includes at least one holding portion for holding the object and the holding portion includes at least one spacer configured such that the object, in the packed state, is held in a contact-free manner with respect to a part of the housing wall of the holding part which extends in the direction of the longitudinal receptacle axis, and wherein
    for removal of the object from the housing, the housing is broken at the predetermined breaking point.

2. The package housing as claimed in claim 1, wherein the predetermined breaking point runs substantially at right angles to the longitudinal axis of the receptacle.

3. The package housing as claimed in claim 1, wherein the predetermined breaking point comprises at least one bridge, which breaks in the case of a predefined bending angle between the head part and the holding part.

4. The package housing as claimed in claim 1, wherein the at least one spacer is configured in the form of a protrusion protruding from the receptacle, which protrusion forms a support surface for the object.

5. The package housing as claimed in claim 4, wherein the protrusion protrudes at the support surface.

6. The package housing as claimed in claim 1, wherein the holding part comprises just a single holding portion.

7. The package housing as claimed in claim 1, wherein the holding portion is disposed in a region adjoining the predetermined breaking point.

8. The package housing as claimed in claim 1, wherein the holding portion holds the object by a snap-locking connection.

9. The package housing as claimed in claim 8, wherein the holding portion comprises two elastic snap-locking lips arranged lying opposite each other about the longitudinal axis of the receptacle.

10. The package housing as claimed in claim 1, wherein the inside of the package housing is sterile.

11. The package housing as claimed in claim 1, wherein the base element comprises an end wall lying in a plane running at right angles to the longitudinal receptacle axis.

12. The package housing as claimed in claim 1, wherein the head part has an end wall having a guide which tapers in the direction of the receptacle and which holds the object by a clamping action.

13. The package housing as claimed in claim 1, wherein at least one of the head part and the holding part is/are configured substantially in the form of a trough.

14. The package housing as claimed in claim 1, wherein the receptacle is covered by a see-through packaging film.

15. The package housing as claimed in claim 1, wherein the elongate object is a drill attachment.

16. A packaging arrangement comprising a package housing as claimed in claim 1, and an elongate object.

17. The packaging arrangement as claimed in claim 16, wherein the object is a drill attachment.

18. The packaging arrangement as claimed in claim 16, wherein the elongate object is a dental drill attachment.

19. The package housing as claimed in claim 1, wherein the elongate object is a dental drill attachment.

* * * * *

UNITED STATES PATENT AND TRADEMARK OFFICE
CERTIFICATE OF CORRECTION

PATENT NO. : 8,261,910 B2
APPLICATION NO. : 12/873515
DATED : September 11, 2012
INVENTOR(S) : Guenter et al.

It is certified that error appears in the above-identified patent and that said Letters Patent is hereby corrected as shown below:

In the Specifications:

Column 4, line 28, delete "X" and delete "shown".

Signed and Sealed this
Thirtieth Day of April, 2013

Teresa Stanek Rea
*Acting Director of the United States Patent and Trademark Office*